United States Patent [19]

Sutherland et al.

[11] Patent Number: 5,214,165
[45] Date of Patent: May 25, 1993

[54] COMPOUNDS USEFUL AS INTERMEDIATES IN THE SYNTHESIS OF SHIKIMIC ACID DERIVATIVES

[75] Inventors: James K. Sutherland, Stockport; William J. Watkins, Macclesfield; George A. Snow, Macclesfield; Gareth M. Davies, Macclesfield, all of United Kingdom

[73] Assignee: Imperial Chemical Industries PLC, London, England

[21] Appl. No.: 933,827

[22] Filed: Aug. 24, 1992

Related U.S. Application Data

[62] Division of Ser. No. 509,802, Apr. 17, 1990, Pat. No. 5,164,382.

[30] Foreign Application Priority Data

Apr. 18, 1989 [GB] United Kingdom ............. 8908700

[51] Int. Cl.$^5$ .................. C07C 317/08; C07C 303/40
[52] U.S. Cl. ................................. 549/433; 549/546
[58] Field of Search .......................... 549/433, 546

[56] References Cited

PUBLICATIONS

Pilch et al, Fluorine–Containing Analogues of Intermediates in the Shikimate, *Biochemistry*, vol. 15, No. 24, pp. 5315–5320, (1976).

Leroy et al, Stereospecific Synthesis of Racemic cis- and trans-6-Trifluoromethylshikimic Acids, *J. Chem. Soc. Perkin Trans. 1*, pp. 1281–1287, (1990).

Bundgarrd "Design of Prodrugs: Bioreversible Derivatives for Various Functional Groups and Chemical Entities", pp. 1 and; 2, *Design of Prodrugs*, Bungaard, ed. (1985) Elsevier Amsterdam.

Le Marechal, "Contribution to the Study of the Mechanism of Action of an Enzyme of the Aromatic Amino Acid biosynthetic Pathway; 3-Dehydroguinate Synthetase from *Escherichia coli*. Preparation and use of Analogues of 3-dexosy-D-arabino heptulosonate 7-phosphate, its substrate.", Thesis submitted at the University of Paris XI, Dentre D'Orsay to obtain the degree of Doctor of Natural Sciences by Pierre Le Marechal (1981).

Ganem, B. *Tetrahedron* 1978, 34 (23), 3353–83.

Bowles et al, "Reactivity Studies in the Shikimic Acid Series", *Tetrahedron Letters*, vol. 30, No. 28, pp. 3711–3714, 1989.

Le Marechal et al, The Shikimate Pathway V, Flourine–containing Analogues of 3-deoxy-D-arabino hept-2-ulsonate-7-phosphate (DAHP) Biochemie 1986, 68, 1211–1215.

*Primary Examiner*—Mary C. Lee
*Assistant Examiner*—Michael G. Ambrose
*Attorney, Agent, or Firm*—Cushman, Darby & Cushman

[57] ABSTRACT

6-Fluoroshikimic acid derivatives of the formula (I):

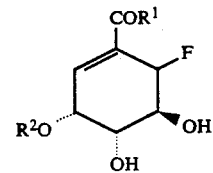

wherein $R^1$ is hydroxy or a moiety biotransformable thereto and $R^2$ is hydrogen or $-P(O)(OH)_2$ have antibacterial, antifungal and herbicidal activity. Their preparation and use are described as are pharmaceutical compositions containing them.

6 Claims, No Drawings

COMPOUNDS USEFUL AS INTERMEDIATES IN THE SYNTHESIS OF SHIKIMIC ACID DERIVATIVES

Edwards (The biosynthesis of aromatic compounds, Wiley, N.Y. (1981)).

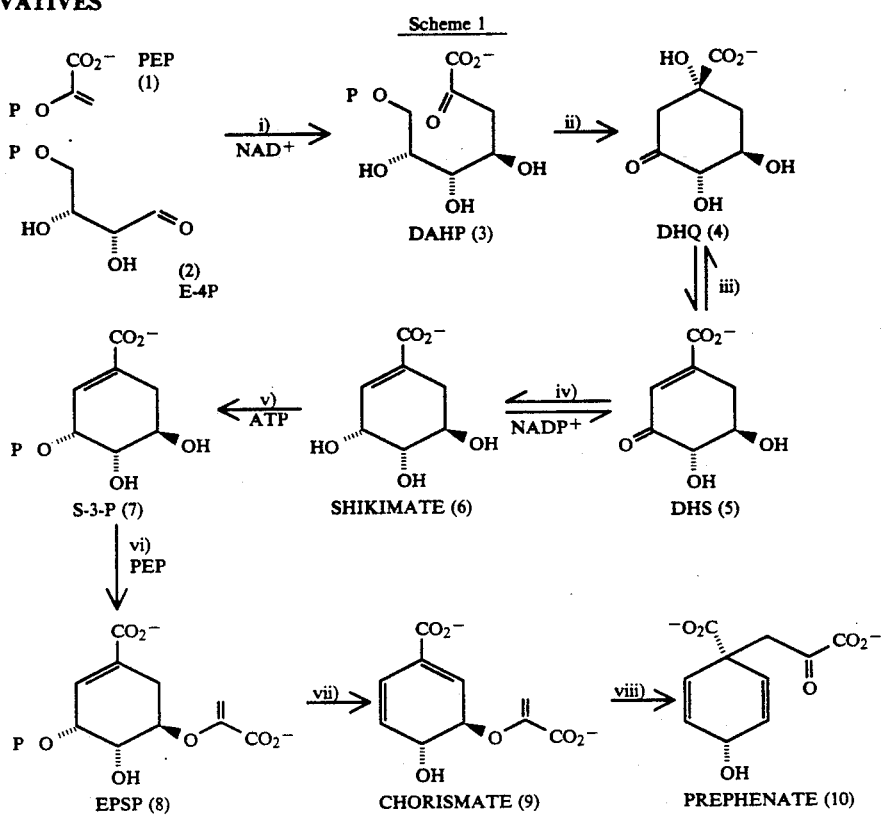

Enzymes:
  i) DAHP synthase;
  ii) 3-dehydroquinate synthase;
  iii) 3-dehydroquinate dehydratase;
  iv) shikimate dehydrogenase,
  v) shikimate kinase;
  vi) EPSP synthase;
  vii) chorismate synthase;
  viii) chorismate mutase.

This is a division of application Ser. No. 07/509,802, filed Apr. 17, 1990, now U.S. Pat. No. 5,164,382.

This invention relates to shikimic acid derivatives and in particular to 6-fluoroshikimic acid derivatives. The invention further relates to compositions containing such derivatives and to their use as antibacterial, antifungal and herbicidal agents. In addition the invention relates to novel processes for their preparation.

The shikimic acid pathway is essential for the existence of bacteria and plants as it provides for the synthesis of the necessary metabolites. In bacteria the pathway provides not only the three aromatic α-amino acids (tyrosine, tryptophan and phenylalanine) but also p-aminobenzoic acid, p-hydroxybenzoic acid, O-succinylbenzoic acid, 2,3-dihydroxybenzoic acid and salicyclic acid, intermediates respectively for the synthesis of the folate co-enzymes, the prenylquinones, vitamin K, the enterochelins and the mycobactins.

The shikimic acid pathway is depicted in Scheme I. Comprehensive reviews include those of Haslam (The Shikimate pathway, Halstead Press, N.Y. (1974), Ganem (Tetrahedron, 34,3353 (1978)) and Weiss and Le Marechal et al (Biochemie, 68, 1211 (1986)) describe that incubation of radiolabelled 3R- or 3S- 3-fluoro DAHP with 3-dehydroquinate synthetase and 3-dehydroquinase from E. coli gave compounds assumed to be respectively the 6R- or 6S-6-fluoro 3-dehydroshikimates of the formula:

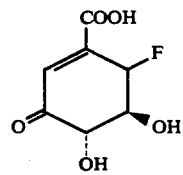

which compounds were not purified further because of their relative propensity to be dehydrated into aromatic derivatives. Le Marechal proceeds to state that spectroscopic evidence has been obtained for the slow conversion of the assumed 6R- or 6S-6-fluoro 3-dehydroshikimates into the corresponding 6-fluoro shikimates in the presence of NADPH and 3-dehydroshikimate reductase from E. coli. Le Marechal et al carried out their investigations in order to use the afore-mentioned (and other) substrate analogues as tools in the determination of the mechanism of enzymes in the aromatic biosynthesis pathway (Scheme I).

Pilch et al (Biochemistry, 15,5315 (1976)) also describe investigations into fluorine containing analogues of intermediates in the shikimate pathway. They describe 3S-fluoro DAHP and the enzymatic conversion thereof into 6S-fluoro DHQ. It is suggested that possible fluorinated intermediates in the shikimate pathway could include 6-fluoroshikimic acid but no description of this compound is given, nor is there any suggestion of any preparation of such a compound. Pilch et al performed their studies in order to obtain mechanistically useful data and to aid the elucidation of substrate specificity in aromatic biosynthesis.

The applicants of the present invention have investigated derivatives of shikimic acid and, unexpectedly, have found that certain fluoro derivatives possess useful antibacterial, antifungal and/or herbicidal activity.

Accordingly the present invention provides a compound of the formula (I):

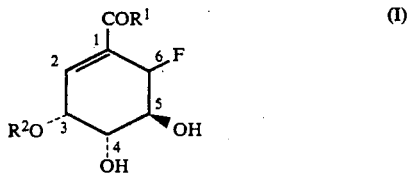

wherein $R^1$ is hydroxy or a moiety biotransformable thereto; and $R^2$ is hydrogen or $-P(O)(OH)_2$; or a pharmaceutically acceptable salt thereof.

$R^1$ is hydroxy or a moiety biotransformable to hydroxy in the human or animal body. Suitable biotransformable moieties include biodegradable esters conventional in the art, for example $R^1$ is $C_{1-6}$alkoxymethoxy, $C_{1-6}$alkanoyloxymethoxy, $C_{1-6}$alkoxycarbonyloxymethoxy or a phthalidyloxy group. Typical groups $R^1$ include methoxymethoxy, acetoxymethoxy and ethoxycarbonyloxymethoxy. In an alternative $R^1$ may be the residue of an amino acid or peptide for example $R^1$ may be D- or L-ala or may be L-ala-L-ala. Such amino acids or peptides are known to aid active transport into bacteria via peptide permeases. The peptide or amino acid is subsequently cleaved by intracellular peptidase.

Preferably $R^1$ is hydroxy.

$R^2$ is hydrogen or $-P(O)(OH)_2$ that is 6-fluoroshikimate-3-phosphate. Preferably $R^2$ is hydrogen.

Suitable pharmaceutically acceptable salts include those with alkali metals for example sodium or potassium, alkaline earth metals for example calcium, ammonium salts and pharmaceutically acceptable organic amines for example triethylamine.

The present invention covers the compounds of the formula (I) as the 6R-isomer, as the 6S-isomer and racemic mixtures thereof.

The compound is preferably in substantially pure form, for example at least 75% pure, preferably at least 90% pure and most preferably at least 95% pure.

Particular compounds of the formula (I) are 6S-fluoroshikimic acid or a derivative thereof, preferably in substantially pure form, and 6R-fluoroshikimic acid or a derivative thereof, preferably in substantially pure form.

The compounds of the formula (I) interfere in the shikimic acid pathway existing in bacteria and plants. They are therefore of use in treating disease conditions wherein the shikimic acid pathway is implicated, in particular they are of use as antibacterial agents, as evidenced by activity in conventional in vitro and in vivo antibacterial tests.

Accordingly in another aspect the present invention provides a compound of the formula (I) or pharmaceutically acceptable salt thereof for use in a method of therapeutic treatment, in particular in a method of antibacterial treatment.

In a further aspect the present invention provides a pharmaceutical composition which comprises a compound of the formula (I) or pharmaceutically acceptable salt thereof and a pharmaceutically acceptable carrier.

In yet a further aspect the present invention provides the use of a compound of the formula (I) or a pharmaceutically acceptable salt thereof for the manufacture of a medicament for the treatment of bacterial infection.

The pharmaceutical compositions of this invention may be administered in a standard manner for the disease condition that it is desired to treat, for example by oral, rectal or parenteral administration. For these purposes the compositions may be formulated by means known to the art into the form of, for example, tablets, capsules, aqueous or oily solutions or suspensions, emulsions, dispersible powders, suppositories and sterile injectable aqueous or oily solutions or suspensions.

In addition to the pharmaceutically acceptable compound of the present invention the pharmaceutical composition of the invention may also contain, or be co-administered with, one or more known drugs selected from other clinically useful antibacterial agents (for example beta-lactams or aminoglycosides), dihydrofolate reductase inhibitors (for example trimethoprim), tubular blocking agents (e.g. probenicid) and inhibitors of metabolising enzymes (for example inhibitors of peptidases, for example Z-2-acylamino-3-substituted propenoates). In a particularly preferred aspect the compounds of the formula (I) show a synergistic activity when co-administered with sulphonamides, either simultaneously, separately or sequentially.

A preferred pharmaceutical composition of the invention is one suitable for intravenous, subcutaneous or intramuscular injection, for example a sterile injectable containing between 1 and 20% w/w of the compound of the formula (I) or one suitable for oral administration in unit dosage form, for example a tablet or capsule which contains between 50 mg. and 3 g. of the compound of the formula (I).

The pharmaceutical compositions of the invention will normally be administered to man in order to combat infections caused by bacteria, in the same general manner as that employed for sulphonamides due allowance being made in terms of dose levels for the potency of the compounds of the present invention relative to the known clinically used sulphonamides. Thus each patient will receive a daily intravenous, subcutaneous or intramuscular dose of 0.05 to 30 g., and preferably 0.1 to 10 g., of the compounds of this invention, the composition being administered 1 to 6 times per day, preferably 1 to 3 times a day. The intravenous, subcutaneous and intramuscular dose may be given by means of a bolus injection. Alternatively the intravenous dose may be given by continuous infusion over a period of time. Alternatively each patient will receive a daily oral dose which is approximately equivalent to the daily parenteral dose. Thus a preferred daily oral dose is 0.5 to 10 g. of the compound of the formula (I), the composition being administered 1 to 4 times per day.

In addition the shikimic acid pathway is implicated in plant growth. Indeed it is though that the herbicide glyphosate is effective through functioning as a phosphonoenolpyruvate (PEP) mimic (see Scheme I). The compounds of the formula (I) have been shown to possess herbicidal properties, as evidenced by activity in the standard carrot cell test in which the well-known herbicide glyphosate is also active.

Accordingly in another aspect of the present invention there is provided a process of inhibiting the growth of unwanted plants, by applying to the plants, or to the locus thereof, a compound of the formula (I) as hereinbefore defined or a salt thereof.

The rate of application required to inhibit the growth of unwanted plants will depend on the particular compound chosen and the particular species of plant that it is desired to control.

The compounds of the formula (I) are preferably applied in the form of a composition. In a further aspect, therefore, the present invention provides a herbicidal composition comprising a compound of the formula (I) or a salt thereof in admixture with a diluent.

Suitable compositions are those conventional in the herbicide art, for example solid compositions (e.g. powders and granules) and liquid compositions (e.g. solutions, dispersions and emulsions). Conveniently surface active agents are included in the compositions. The herbicidal compositions of this invention are formulated in conventional manner with conventional diluents appropriate to the mode of application.

The compounds of the formula (I) and salts thereof have anti-fungal properties. Thus they may be useful in situations where anti-fungal activity is desired for example they are useful in pharmaceutical preparations, in veterinary preparations, as agrochemicals and as industrial fungicides. The present invention, therefore, includes the above-mentioned fungicidal uses of the compounds of the formula (I) and their salts.

Conveniently the compounds of the formula (I) and their salts, for fungicidal use, are formulated into compositions in a manner conventional for the required use. Accordingly the invention further provides a fungicidal composition comprising a compound of the formula (I) or a salt thereof and a diluent therefor.

For pharmaceutical or veterinary administration the composition of the invention conveniently is in a form, suitable for oral administration (e.g. a tablet, capsule, an emulsion or suspension) or suitable for topical application (e.g. a cream, ointment or gel).

In another aspect of the present invention there is provided a process for preparing a compound of the formula (I) which comprises reacting a compound of the formula (II):

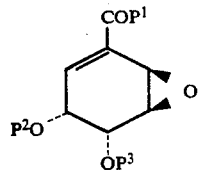

(II)

wherein
P$^1$ is a group R$^1$ or a protected derivative thereof; and
P$^2$ and P$^3$ are protecting groups, with a source of fluoro and subsequently removing any protecting group and, if necessary:

i) converting a compound wherein R$^1$ is hydroxy to a compound wherein R$^1$ is a moiety biotransformable thereto,
ii) converting a compound wherein R$^2$ is hydrogen to a compound wherein R$^2$ is —P(O)(OH)$_2$,
iii) forming a pharmaceutically acceptable salt.

A convenient source of fluoro is a mineral acid, that is hydrofluoric acid. Conveniently the reaction of the epoxide of the formula (II) with the mineral acid is performed in the presence of an organic base for example pyridine. The reaction can be performed in any substantially inert solvent in particular halogenated hydrocarbons such as dichloromethane and chloroform. The reaction can be performed at any non-extreme temperature, more particularly between 0° C. and ambient temperature and typically at about 0° C.

The compound of the formula (II) is novel and, as such, forms part of the present invention.

The reaction of the epoxide of the formula (II) with the source of fluoro gives the compound of the formula (III):

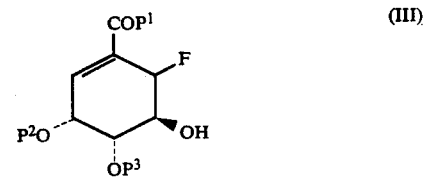

(III)

wherein P$^1$, P$^2$ and P$^3$ are as hereinbefore defined. The compound of the formula (III) is deprotected to give the compound of the formula (I). Thus in another aspect of the invention therein provided a process of deprotecting a compound of the formula (III) to form a compound of the formula (I).

Suitable protecting groups, P$^1$, P$^2$ and P$^3$ can be chosen from any of the groups described in the literature or known to the skilled chemist as appropriate for the protection of the group in question, and may be introduced by conventional methods.

Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Specific examples of protecting groups are given below for the sake of convenience, in which "lower" signifies that the group to which it is applied preferably has 1–4 carbon atoms. It will be understood that these examples are not exhaustive. Where specific examples of methods for the removal of protecting groups are given below these are similarly not exhaustive. The use of protecting groups and methods of deprotection not specifically mentioned is of course within the scope of the invention.

A carboxyl protecting group may be the residue of an ester-forming aliphatic or araliphatic alcohol or of an ester-forming phenol or silanol (the said alcohol, phenol or silanol preferably containing 1–20 carbon atoms).

Examples of carboxyl protecting groups include straight or branched chain (1–12C)alkyl groups (e.g. isopropyl, t-butyl); halo lower alkyl groups (e.g. 2-iodoethyl, 2,2,2-trichloroethyl); lower alkoxy lower alkyl groups (e.g. methoxymethyl, ethoxymethyl, isobutoxymethyl); lower aliphatic acyloxy lower alkyl groups, (e.g. acetoxymethyl, propionyloxymethyl, butyryloxymethyl, pivaloyloxymethyl); lower alkoxycarbonyloxy lower alkyl groups (e.g. 1-methoxy-carbonyloxyethyl, 1-ethoxycarbonyloxyethyl); aryl lower alkyl groups (e.g. p-methoxybenzyl, o-nitrobenzyl, p-nitrobenzyl, benzhydryl and phthalidyl); tri(lower alkyl)silyl groups (e.g. trimethylsilyl and t-butyldimethylsilyl); tri(lower alkyl)silyl lower alkyl groups (e.g. trimethylsilylethyl); and (2-6C)alkenyl groups (e.g. allyl and vinylethyl).

Methods particularly appropriate for the removal of carboxyl protecting groups include for example acid-, base-, metal- or enzymically-catalysed hydrolysis.

Examples of hydroxyl protecting groups include lower alkanoyl groups (e.g. acetyl); lower alkoxycarbonyl groups (e.g. t-butyoxycarbonyl); halo lower alkoxycarbonyl groups (e.g. 2-iodoethoxycarbonyl, 2,2,2-trichloroethoxycarbonyl); aryl lower alkoxycarbonyl groups (e.g. benzoyloxycarbonyl, p-methoxybenzyloxycarbonyl, o-nitrobenzyloxycarbonyl, p-nitrobenzyloxycarbonyl); tri lower alkylsilyl (e.g. trimethylsilyl, t-butyldimethylsilyl) and aryl lower alkyl (e.g. benzyl) groups. In addition two hydroxy groups substituted on adjacent carbon atoms, for example $P^2O-$ and $P^3O-$, may be protected in the form of a cyclic acetal such as the methylene dioxy, benzylidene or cyclohexylidene moieties.

The protecting group $P^1$ may be a suitable biodegradable ester and, if it is desired to form a compound of the formula (I) in the form of a biodegradable ester then clearly it is not necessary to remove the group $P^1$.

The compound of the formula (II) can be prepared by reacting a compound of the formula (IV):

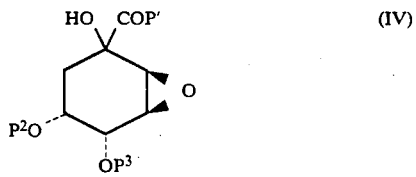

wherein $P^1$, $P^2$ and $P^3$ are as hereinbefore defined, with a dehydrating agent, for example, Martins reagent, phosphorus oxychloride or sulphuryl chloride in pyridine. Conveniently the reaction is performed in a solvent such as a halogenated hydrocarbon for example dichloromethane. Typically the reaction is performed at a low temperature for example at about $-78°$ C.

The compounds of the formula (IV) can be prepared from quinic acid by the methods described in Descriptions 1-9 (vide infra), due allowance being made for the preparation of compounds of the formula (IV) with other protecting groups as the skilled man will realise.

The compound of the formula (I) wherein $R^1$ is hydroxy and $R^2$ is $-P(O)(OH)_2$ (6-fluoroshikimate-3-phosphate) may be prepared from 6-fluoroshikimic acid (the compound of the formula (I) wherein $R^2$ is hydrogen) by treatment with a suitable enzyme preparation. The enzyme preparation for example may be a broken cell preparation or a purified enzyme. An example of a suitable enzyme is Shikimate kinase. Typically the 6-fluoroshikimic acid is incubated with the enzyme at a temperature of about 37° C. in a pH8 buffered mixture containing adenosine triphosphate (ATP). 6-Fluoroshikimate-3-phosphate may be converted to a corresponding salt in conventional manner.

The following Biological Test Methods and Data, Descriptions and Example serve to illustrate the invention.

BIOLOGICAL TEST METHODS AND DATA

1) Antimicrobial activity was assessed in vitro using a disc diffusion method and a method wherein the test compound was in agar. Both methods employed the use of Davis and Mingioli (J. Bact (1950) 60 17-28) glucose agar.

i) The disc diffusion method used an overnight culture of *E. coli* N99 in Davis and Mingioli broth as an ioculum for the agar (e.g. 500 µl/100 ml agar). Test compounds were dissolved in distilled water and placed on to a 6 mm diameter disc which had just been applied to the agar surface. The plates were then incubated for 16 hours at 37° C. Using this method the following zones of inhibition were observed.

| Test compound | Amount applied on to disc (µg) | mm diameter zones of inhibition vs. *E. coli* N99 |
| --- | --- | --- |
| 6-β-fluoroshikimate | 1.5 | 0 |
| " | 3.0 | 13.0 very hazy |
| " | 30.0 | 26.0 very hazy |
| 6-α-fluoroshikimate | 0.025 | 0 |
| " | 0.05 | 10.0 hazy |
| " | 1.5 | 29.0 hazy, 23.0 inner clear | ii) The "test compound in agar" method studied 6-α-fluoroshikimate at various final concentration in the agar (i.e. between 0 and 500 µg/ml) to obtain MIC (minimum inhibitory concentration) values for nine different bacterial cultures. Cultures were grown in Davis and Mingioli broth for 16 hours at 37° C. and diluted in fresh Davis and Mingioli broth to give $10^6$ cells/ml. 1 µl volume of each culture was applied to the surface of each agar plate containing 6-α-fluoroshikimate and the plates were then incubated for 16 hours at 37° C. before each inoculation spot was visually assessed for growth. Using this technique the following results were observed:

| Culture Name | MIC µg/ml |
| --- | --- |
| *E. coli* B | 1.0 |
| *E. coli* N99 | 0.1 |
| *Klebsiella pneumoniae* | 5.0 |
| *Klebsiella pneumoniae* ATCC 25304 | 1.0 |
| *Enterobacter cloacae* | 50.00 |
| *Pseudomonas aeruginosa* 799/wt | >500.0 |
| *Bacillus subtilis* | 50.00 |
| *Bacillus licheniformis* | >500.0 |
| *Serratia marcescens* | >500.0 |

2) Reversal studies were performed by adding agents to an *E. coli* N99 (Davis and Mingioli broth) $10^6$ cells/ml. suspension in the presence of 6α-fluoroshikimate and the bacterial growth assessed by the use of a spectrophotometer (Absorbance 540 nm)

Inhibition of bacterial growth was reversed by paraaminobenzoic acid (PABP) but degrees of counter reversion were seen after the addition of aromatic amino acid types. Using this technique the following results were observed:

| Agent added | μg/ml Final well concentration | Effect on the *E. coli* N99 inhibited growth (+, ++, +++, ++++ indicate the extent of growth) |
| --- | --- | --- |
| PABA | 0.1 | Full reversion of inhibition (++++) |
| PABA | 100.0 | Full reversion of inhibition (++++) |
| L-Phenyl alanine | 100.0 | No reversion of inhibition |
| L-tyrosine | 100.0 | No reversion of inhibition |
| L-tryptophan | 100.0 | No reversion of inhibition |
| PABA + L-phe | both at 100.0 | No reversion of inhibition |
| PABA + L-tyr | both at 100.0 | Some reversion of inhibition (+) |
| PABA + L-trp | both at 100.0 | Some reversion of inhibition (++) |
| PABA + L-phe L-tyr + L-trp | all at 100.0 | Some reversion of inhibition (+++) |

3) The interaction of 6-fluoroshikimate (racemic mixture) with a representative sulphonamide (sulphamethoxazole) was tested using both a disc approximation method and chequerboard titration. The former method gave evidence of a synergistic interaction against a strain each of *Enterobacter cloacae*, *Klebsiella pneumoniae* and *E. coli* K12. The synergistic interaction was confirmed for *E. coli* K12 by chequerboard titration.

4) The in vivo efficacy of the fluoroshikimate was determined by the use of a mouse protection test. Male mice (18–20 g) were inoculated intraperitoneally with ten times the previously determined LD$_{50}$ for *E. coli* N99 in 0.4 ml of hog gastric mucin (12%). Immediately after infection the mice were dosed with 0.2 ml of test compound either subcutaneously, per os or intraperitoneally. Based on the number of survivors at day 4 post infection, PD$_{50}$ values were calculated by LOGIT analysis.

| 6-α-Fluoroshikimate | PD$_{50}$ (day 4) per os | subcutaneous | intraperitoneal |
| --- | --- | --- | --- |
| *E. coli* N99 | 8.6 | 4.6 | >10 |
| *E. coli* 341094 | 13.4 | 23.2 | |
| *S. aureus* 601055 | 20 | 20 | |
| *S. dublin* 369001 | 50 | 20 | |

All control animals died by 24–40 hours post infection.

5) In a standard test for herbicidal activity carrot cells were grown in shake flasks at 25° C. in liquid culture (Murashige and Skoog media with 0.2 mg/liter of kinetin and 0.1 mg/liter of 2.4 dichlorophenoxyacetic acid). The growth of cells was measured and an IC$_{50}$ value obtained for compounds which were added in water. The IC$_{50}$ value for 6-fluoroshikimate (racemic mixture) was 1.5 μ/ml; evidence of herbicidal activity.

DESCRIPTIONS AND EXAMPLES

Melting Points were determined on a Kofler block and are uncorrected.

Reaction solvents

Diethyl ether and tetrahydrofuran were dried by standing over potassium hydroxide and then refluxing with sodium/benzophenone.

Absolute methanol was dried by refluxing with and distilling from magnesium methoxide.

Pyridine was dried over KOH.

Dimethylformamide and benzene were dried over and distilled from calcium hydride.

Dichloromethane and chloroform were distilled from CaH$_2$ or (for small amounts) passed down a column of Al$_2$O$_3$ (Activity 1).

Abbreviations

Ether = diethyl ether

EtOAc = ethyl acetate

DBU = 1,8-Diazabicyclo[5.4.0]undec-7-ene

DMF = N,N-dimethylformamide hplc = high performance liquid chromatography

THF = tetrahydrofuran

TFA = trifluoroacetic acid

Petrol = 40–60 petrol (distilled before use)

Usual work-up refers to extraction with dichloromethane, washing of the combined organic solutions with saturated brine, drying over MgSO$_4$, filtration, and evaporation of the solvents in vacuo.

DESCRIPTION 1

1S,3R,4R,5R)
3,4-O-Cyclohexylidene-7-oxo-6-oxabicyclo-[3.2.1]octan-1,3,4-triol

A mixture of quinic acid (25.0 g, 0.13 mol), cyclohexanone (88 ml, 0.85 mol), DMF (105 ml) and benzene (100 ml) was heated at reflux in an apparatus fitted with a Dean-Stark trap. After 150 minutes no further water was separated; the mixture was cooled briefly and dried Amberlite resin IR 120(H) (21.5 g) was added. The suspension was heated at reflux for 7 hours. After cooling overnight, the resin was removed by filtration. The filtrate was cooled to 0° C. and washed with ice-cold sodium bicarbonate solution (5% aq., 2×25 ml) and brine (1×25 ml). The filtrate was dried (Na$_2$SO$_4$) and concentrated at high vacuum to give a yellow solid which was triturated with hexane. The title compound was recovered as a white solid. The mother liquors were concentrated and retriturated; the total yield of product was 24.98 g (75.6%). Recrystallisation from ether gave colourless needles M.Pt. 140°–141° C. $[\alpha]_D^{20} = -29.4°$ (c0.435, CHCl$_3$). Combustion analysis: C$_{13}$H$_{18}$O$_5$ requires C 61.4%, H 7.1%; found C 61.5%, H 7.3%. R$_f$ 0.20 (30% EtOAc/C$_6$H$_{12}$). NMR (200 MHz, CDCl$_3$): δ1.25–1.80(10H,m); 2.18(1H, dd, J=15, 3Hz); 2.23–2.45(2H,m); 2.67(1H, dd, J= 12.5 Hz); 3.0(1H, br s, exch.D$_2$O); 4.05(1H,m); 4.49(1H,m, J=3.2, 6.4, 6.6 Hz); 4.74(1H, dd, J=3, 6.4 Hz). IR(CHCl$_3$): γ$_{max}$ 3040(br,m); 2980(m), 1780(s), 1450(m), 1340(w), 1305(w), 1280(m) cm$^{-1}$. MS(EI): 254(M$^+$), 225(M$^+$ −CHO), 211(100%; M$^+$−CO$_2$+1).

DESCRIPTION 2

(1S,3R,4R,5R)
1-O-Benzyloxycarbonyl-3,4-0-cyclohexylidene-7-oxo-6-oxabicyclo[3.2.1]octan-1,3,4-triol.

The lactone from Description 1 (3.0 g, 11.8 mmol) was dissolved in dichloromethane (110 ml) and cooled with stirring to 0° C. Sodium hydride (520 mg, 60% suspension in paraffin, 13 mmol) was added as a suspension in dichloromethane (10 ml) to give a flocculent suspension. Benzyl chloroformate (2.53 ml, 17.7 mmol) was added dropwise over 5 minutes, during which time the mixture changed color from orange to yellow. Tetrabutylammonium iodide (50 mg) was added the mixture was stirred for 54 hours. Water (20 ml) was added, and the usual work-up applied. The resulting oil could be dissolved in hot ethyl acetate and the title compound recovered as colorless needles from the cooled solution. Residual product in the mother liquor was recovered by dry column chromatography (15% EtOAc/petrol), $R_f$ 0.35 (20% EtOAc/petrol). The yield of the title compound was 4.32 g (94%). Analytically pure material was obtained by recrystallisation from ether, M.Pt. 97°–98° C. $[\alpha]_D^{20}= +5.67°$ (c1.34, $CH_2Cl_2$). Combustion analysis: $C_{21}H_{24}O_7$ requires C 64.94%, H 6.23%, found C 65.15%, H 6.5%. NMR (60 MHz, $CDCl_3$): δ1.3–1.8(10H,m); 2.3–2.5(3H,m); 2.8(1H,d, J=11 Hz, 4.3.4.55(2H,m); 4.75(1H,m); 5.10(2H,ms); 7.25(5H,s). IR(TF): $\gamma_{max}$ 3035(w), 2937(s), 2861(m), 1807(s), 1756(s), 1599(w), 1499(m), 1455(m), 138(m), 1336(m), 1266(s), 1164(s), 1114(m), 1088(s), 1044(m), 1007(m) $cm^{-1}$. MS(EI): 388(M+), 345(M+—$C_3H_7$), 325, 91($C_6H_5CH_2$), 57(100%: $C_4H_9$).

DESCRIPTION 3

Methyl 1-benzyloxycarbonyl-3,4-O-cyclohexylidenequinate

Treatment with sodium methoxide solution was used to transform the lactone from Description 2, (10.71 g, 27.6 mmol) to the product. The title compound (10.77 g, 93%) was isolated as a white crystalline solid. Recrystallisation from ether gave colourless needles, M.Pt. 139°–140° C. $[\alpha]_D^{20}= -13.6°$ (c1.91, $CH_2Cl_2$). NMR (300 MHz, $CDCl_3$): δ1.3–1.8(10H,m); 1.87(1H, dd, J=14.0, 10.5 Hz), 2.19(1H, dm, J=14.0 Hz), 2.33(1H, dd, J=16.0, 5.0 Hz); 2.43 (1H, br s), 2.70(1H, dm, J=16.0 Hz), 3.66(3H, s), 3.90(1H, dd, J=6.0, 5.0 Hz), 4.04(1H, m), 4.35(1H,m), 5.13(2H, abq, J=12 Hz), 7.33(5H,s), IR(TF): $\gamma_{max}$ 3443(br,m), 2936(s), 2850(m), 1747(s), 1499(w), 1450(m), 1383(m), 1284(s), 1230(s), 1166(m), 1122(m), 1095(m), 1048(m) $cm^1$. MS(EI): 420(M+), 388(M+—OMe), 377(M+—$C_3H_7$), 359(M−—OMe—$C_2H_5$), 345(M+—OMe—$C_3H_7$), 91(100%; $C_6H_5CH_2$). $C_{22}H_{28}O_8$ requires M+420.1784; found 420.1786.

DESCRIPTION 4

(1R,4S,5R) 1-O-Benzyloxycarbonyl-4,5-O-cyclohexylidene-1-methoxycarbonylcyclohex-2-en-1,4,5-triol The alcohol from Description 3 (10.60 g, 25.4 mmol) was dissolved in pyridine (5.2 ml, 63 mmol) and dichloromethane (350 ml), and the solution was cooled to −15° C. (ice/MeOH bath) under an atmosphere of dry $N_2$. Trifluoromethanesulphonic anhydride (6.66 ml, 40 mmol) was added dropwise over 5 minutes. The flask was allowed to warm to room temperature and after 1 hour saturated $NH_4Cl$ solution (75 ml) was added. The usual work-up gave a thick oil from which the pyridine was removed by evaporation of a toluene solution. The resulting oil was dissolved in chloroform (150 ml) and DBU (6.56 ml, 42 mmol) was added dropwise. The mixture was heated at reflux for 3 hours. After cooling the solvent was removed at reduced pressure and the residue purified by dry column chromatography (gradient elution, 10% EtOAc/petrol to 30% EtoAc/petrol) to give the title compound as a clear oil (8.82 g, 86%). NMR (60 MHz, $CDCl_3$): δ1.3–1.8(10H,m); 2.12(1H, dd, J=13.0, 7.0Hz), 2.58(1H, dd, J=13, 5 Hz), 3.70(3H, s), 4.50(2H,m); 5.10(2H, s); 6.03(2H, s); 7.30(5H, s). IR(TF): $\gamma_{max}$ 2936(m), 2860(m), 1747(s), 1499(w), 1450(m), 1381(m), 1289(s), 1164(m), 1115(m), 1087(s), 1045(m), 1013(m) $cm^{-1}$. MS(EI): 402(M+), 359(M+—$C_3H_7$), 345(M+—$C_4H_9$), 251(M+—BuOCO), 91(100%; $PhCH_2$). $C_{22}H_{26}O_7$ requires M+ 402.1999; found 402.2000.

DESCRIPTION 5

(1R,4S,5R) 1-Hydroxy-1-carboxylic acid-4,5-O-cyclohexylidenecyclohex-2-en-1,4,5-triol The ester from Description 4 (24.4 g, 0.06 mol), aq.-KOH (34 g in 50 ml $H_2O$, 0.6 mol) and 1,4-dioxan (120 ml) were stirred at room temperature overnight. The solvents were evaporated and the residue azeotroped with toluene. The resulting waxy solid was triturated with hexane to give the title compound as a cream solid (51.7 g crude) one spot tlc (30% MeOH, 70% $CH_2Cl_2$). MS (EI): 254(M+); 225(M+—$C_2H_5$); 211(M+—$C_3H_7$).

DESCRIPTION 6

(1S,4S,5R)(1-O-Acetyl)-1-carboxylic acid-4,5-O-cyclohexylidenecyclohex-2-ene-1,4,5-triol The crude hydroxy acid from Description 5 (51.7 g) suspended in dichloromethane (100 ml) was cooled to 0° C. and acetic anhydride (33 ml) added followed by pyridine (33 ml). The mixture was stirred at room temperature overnight. The mixture was evaporated, diluted with EtOAc (200 ml) and ice (200 ml), extracted with EtOAc then diluted with brine and extracted with n-butanol. The organic extracts were dried over $MgSO_4$ and evaporated to give the title compound an oil (24.6 g crude) tlc (9% MeOH, 90% $CH_2Cl_2$, 1% HOAc). MS (EI) 296(M+); 267(M+—$C_2H_5$); 253(M+—$C_3H_7$).

DESCRIPTION 7

(1S,3R,4R,5R,6R)1-(O-Acetyl)-5-bromo-3,4-cyclohexylidene-8-oxo-7-oxabiocyclo[4.2.0$^{1,6}$]octane-1,3,4-triol.

The crude alkene from Description 6 (24.5 g, 0.082 mol) was dissolved in THF (89 ml) and saturated aqueous sodium bicarbonate (360 ml) and treated dropwise with a solution of pyridinium bromide perbromide (29.4 g, 0.09 mol) in THF (90 ml). Dichloromethane (300 mls) was then added and the mixture stirred for 3hrs before being diluted with saturated brine (400 ml) and extracted with EtOAc. The residue obtained after evaporating the EtOAc was azeotroped with toluene to give an oil which gradually solidified. Trituration with hexane gave the title compound as a pale brown solid (17.1 g, 55%). A small sample was recrystallised from ethanol. M.pt. 135°–136.5° C. Combustion analysis $C_{15}H_{19}O_6Br$ requires C. 48.0%; H 5.1% found C, 47.4%; H 5.0%. NMR (250 MHz, $CDCl_3$): δ 1.3–1.8(10H,m); 2.2(3H,m); 2.22(1H,dd, J=14.5 Hz, 4.8 Hz); 2.57(1H,dd, J=14.5 Hz, 5.3 Hz); 4.32(1H,dd, J=5.86 Hz, 3.42 Hz); 4.55(1H,ddd, J=7.81 Hz, 3.42 Hz); 5.88(1H,d,J=5.86 Hz); $^{13}C$ NMR=20.32; 23.09; 23.35; 24.94; 29.55; 32.81; 35.92; 45.3; 70.87; 73.08; 77.42; 84.24; 110.16; 166.65; 169.43; MS (EI) 376(M+); 347(M+—$C_2H_5$); 331(M+—$C_3H_7$).

DESCRIPTION 8

(1R,2R,3S,5R,6R)1-Bromo-5,6-cyclohexylidene-3-methoxycarbonylcyclohexan-2,3,5,6-tetraol The β-lactone from Description 7 (36.5 g, 0.097 mol) was dissolved in hplc grade methanol (370 ml) and dried dichloromethane (370 ml ) under an atmosphere of argon, and cooled to 0° C. Sodium methoxide was generated by the addition of sodium (2.5 g, 0.11 mol) to methanol (185 ml) and the resulting solution added to the substrate solution keeping the temperature below 0° C. After 15 minutes saturated NH$_4$Cl (350 ml) and H$_2$O (600 ml) was added. The usual work-up gave a cream foam which was dissolved in CH$_2$Cl$_2$:EtOAc (50:50) and after chromatography on silica, the appropriate fractions were evaporated to give a thick oil which crystallised on standing. The crystals were filtered off and washed with hexane to give the title compound (31.5 g). The mother liquors were evaporated and the residue recrystallised from ET$_2$O/petrol to give the title compound (0.88 g, 91%) M.pt. 130°–131° C. Combustion analysis: C$_{14}$H$_{21}$BrO$_6$ requires C 46.0%, H 5.7%; found C 45.7%, H 5.7: NMR (250 MHz, CDCl$_3$): δ 1.3–1.8(10H,m); 2.02(1H,dd, J=14.4 Hz, 7 Hz); 2.1 (3H,s); 2.95(1H,dd, J=14.4 Hz, 5.5 Hz); 3.75(3H,s); 4.22(1H,dd, J=11.05 Hz; 4 Hz); 4.34(1H,d, J=11.05 Hz); 4.5(1H,dd, J=5 Hz, 4 Hz); 4.62(1H,ddd, J=7 Hz, 5.5 Hz, 4 Hz). MS (EI) 364(M+), 335(M+—C$_2$H$_5$), 321 (M+—C$_3$H$_7$).

DESCRIPTION 9

(1S,2S,4R,5R,6S) 4,5-O-Cyclohexylidene-2-methoxycarbonyl-7-oxabicyclo[4.1.0]heptan-2,4,5-triol The bromohydrin from Description 8 (64.09 g, 0.176 mol) was dissolved DMF (900 ml) and tetra-$^n$butylammonium acetate (52.86 g, 0.176 mol) was added. The mixture was heated at 110° C. for 1½ hours. The usual work up gave a brown oil. Purification by column chromatography on silica (30% EtOAc/petrol) gave the title compound as a white solid. Recrystallisation from petrol/EtOAc gave colourless needles (31.57 g, 63%). Combustion analysis C$_{14}$H$_{20}$O$_6$ requires C 59.2%, H 7.0% found C59.4%, H 7.0% NMR (250 MHz.CDCl$_3$)δ 1.3–1.8(10H,m); 2.1(1H,dd, J=14.3 Hz); 2.25(1H,dd, J=14.3 Hz, 3 Hz); 3.12(1H,dd, J=4 Hz); 3.4(1H,dd, J=4 Hz); 3.7(3H,s); 4.4(2H ,m). MS (BELT CI), 285 ((M+H)+).

DESCRIPTION 10

(1R,2R,3R,6R)2,3-O-Cyclohexylidene-4-methoxycarbonyl-7-oxabicyclo[4.1.0]hept-4-en-2,3-diol The alcohol from Description 9 (7.88 g, 0.028 mol) was dissolved in dichloromethane (50 ml) and added dropwise to a solution of Martins Reagent* (20.73 g, 0.031 mol) in dichloromethane (190 ml) at −70° C. under an atmosphere of argon. After 10 minutes the mixture was allowed to warm to room temperature. After 3½ hours the solvent was evaporated to give a yellow oil. Column chromatography (10% EtOAc/CH$_2$Cl$_2$) gave the title compound, a yellow oil (4.34 g, 59%). NMR (200 MHz,CDCl$_3$)δ 1.3–1.8(10H,m); 3.6(1H,dd, J=3.3 Hz, 1.6 Hz); 3.85(3H,s); 4.0(1H ,dd, J=3.3 Hz, 1 Hz); 4.57(1H,dd, J=6.6 Hz, 1.5 Hz); 4.8(1H,dd, J=6.6 Hz, 1.3 Hz); 6.82(1H,dd). MS (EI), 266(M+), 237(M+—C$_2$H$_5$), 223(M+—C$_3$H$_7$); 152(M+—C$_6$H$_{10}$O$_2$).

*bis[α,α-Bis(trifluoromethyl)benzenemethanolato]-diphenyl sulphur ([C$_6$H$_5$C(CF$_3$)$_2$O]$_2$S(C$_6$H$_5$)$_2$).

DESCRIPTION 11

(3R,4R,5S,6S)Methyl (5-hydroxy)-3,4-O-cyclohexylidene-6-α-fluoroshikimate

The epoxide from Description 10 (6.35 g, 0.024 mol), dissolved in dichloromethane (25 ml) was added dropwise to a rapidly stirred mixture of dichloromethane (55 ml) and 70% HF/pyridine (1.6 ml) under an atmosphere of argon, at room temperature. After 5 minutes the stirring was stopped, the mixture was allowed to separate, the dichloromethane layer removed, and loaded directly onto a silica column (gradient elution 50% Et$_2$O/petrol 100% Et$_2$O 5% MeOH/Et$_2$O). The title compound was thus recovered as a colourless oil (2.25 g, 35%). Also recovered from the column was a mixture of methyl (5-hydroxy-3,4-0-cyclohexylidene-6-fluoroshikimate and other material. This was applied to a C$_{18}$ Dynamax hplc prep column (eluted with 50% CH$_3$CN/H$_2$O) to give the 6-β-fluoroshikimate as a colourless oil (0.33 g, 5%). Title compound. NMR (250 MHz, C$_6$D$_6$)=δ 1.1–1.8 (10H,m); 3.3(3H,s); 4.16(1H,dd, J=5.49 Hz, 5.28 Hz); 4.25(1H,dm, J=12 Hz); 4.43(1H,dt, J=5.49 Hz, 2.96 Hz, 3.42 Hz); 5.3(1H,dd, J=43.7 hz, 3.97 Hz); 6.9(1H,dd, J=3.08 Hz, 2.96 Hz).

6-β-Fluoroshikimate NMR (250 MHz, C$_6$D$_6$, TCAI)=δ 1.3–1.8(10H,m); 3.3(3H,s); 4.3(1H,m); 4.5(1H,dd, J=9.3 Hz, 6.6 Hz); 5.15(1H,ddd, J=25.5 Hz, 9.3 Hz, 2.5 Hz); 5.65(1H,dd, J=50.2 Hz, 2.5 Hz); 7.0(1H,dd, J=3.83 Hz, 3.82 Hz)

EXAMPLE 1

(3R,4R,5S,6S)6-α-Fluoroshikimic acid

The fluoroshikimate from Description 11 (2.15 g, 7.5mmol), trifluoroacetic acid (15 ml), dichloromethane (30 ml) and H$_2$O (0.5 ml) were stirred at room temperature. After 10 minutes the mixture was partitioned between H$_2$O (50 ml) and CCl$_4$ (50 ml) and the aqueous layer evaporated to give a gum. This was dissolved in H$_2$O (40 ml) and HCl (40 ml) and stirred at 60° C. for 7 hours. The mixture was evaporated to give a cream foam. Chromatography on a C$_{18}$ Dynamax reverse phase prep hplc column (eluted with 99.9% H$_2$O/0.1% TFA) followed by trituration with EtOAc resulted in the title compound (0.956 g). Recrystallisation from glacial acetic acid (3 ml) at 90° C. gave white crystals (0.85 g, 59%) M.pt. 165°–6° C. Combustion analysis: C$_7$H$_9$F$_1$O$_5$ requires C 43.8%, H 4.7%; found C 43.6%, H 4.7%. NMR (250 MHz, D$_2$O)δ 3.85(1H,dd, J=9.2 Hz, 4 Hz); 4.2(1H,m); 4.54(1H,m); 5.3(1H,dd, J=48.1 Hz, 5.64 Hz); 7.1(1H,d, J=4.7 Hz). $^{13}$C NMR (62.9 MHz, D$_2$O) 64.37(J=1.5 Hz); 67.62 (J=7.67 Hz); 69.06(J=20.82 Hz); 88.75(J=169.65 Hz); 128.834 (J=18.1 Hz); 129.742(J=6.16 Hz); 167.259. MS (CI), 210(M+NH$_4$)+), 192((M+NM$_4$)+—H$_2$O) 190(M+NH$_4$)+—HF).

EXAMPLE 2

(3R,4R,5S,6R)6-β-Fluoroshikimic acid

Lithium hydroxide (26mgs 1.08mmol) in H$_2$O (0.5 ml) was added dropwise to a solution of the 6-β-fluoroshikimate from Description 11 (178mgs 0.62mmol) in H$_2$O (3 ml) and 1,4-dioxan (2 ml) under an atmosphere of argon. After 1hr. the mixture was partitioned between EtOAc and H$_2$O and the aq. layer freeze dried. The freeze dried gum was stirred at room temperature in dichloromethane (1.25 ml) with H₂O (1 drop) and trifluoroacetic acid (0.6 ml). After 1hr. the dichloromethane layer was extracted and evaporated. Chromatography on a $C_{18}$ Dynamax reverse phase prep hplc column )eluted (a) 20% $CH_3CN/79.9\%$ $H_2O/0,1\%$ TFA and (b) 99.9% $H_2O/0.1\%$ TFA) resulted in the title compound (48mgs, 40%). NMR (250, $D_2O$); δ 4.05(1H,m, J=3.87 Hz); 4.1(1H,m, J=2.93 Hz); 4.6(1H,m, J=4.39 Hz, 3.87 Hz); 5.54(1H,dd, J=2.93 Hz, 50.1 Hz); 7.23(1H,dd, J=4.39 Hz, 4 Hz); $^{13}C$ NMR (62.9 MHz, $D_2O$) 65.34; 67.43; 67.29 (J=22.52 Hz); 86.28 (J=168.57 Hz); 128.36 (J=15.16 Hz); 143.37 (J=6.92 Hz); 168.172. MS (CI) 210 $(M+NH_4)^+$); 192$((M+NH_4)^+-H_2O)$; 190$((M+NH_4)^+-HF)$. For convenience the Descriptions and Examples are depicted in schematic form in Scheme 2.

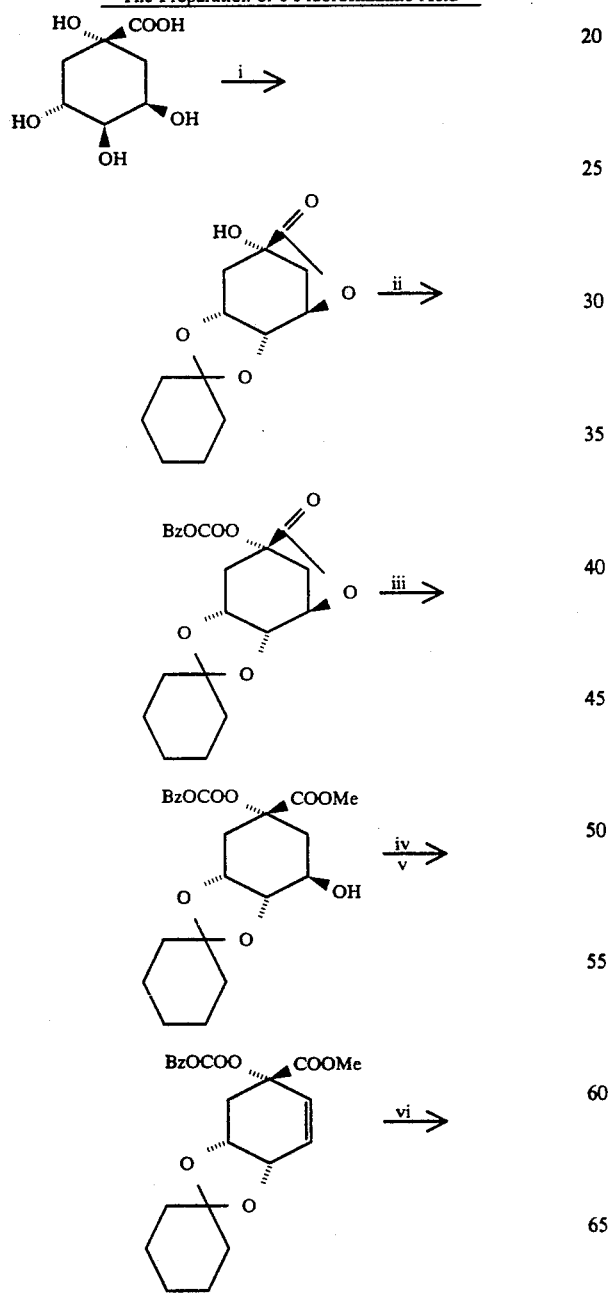

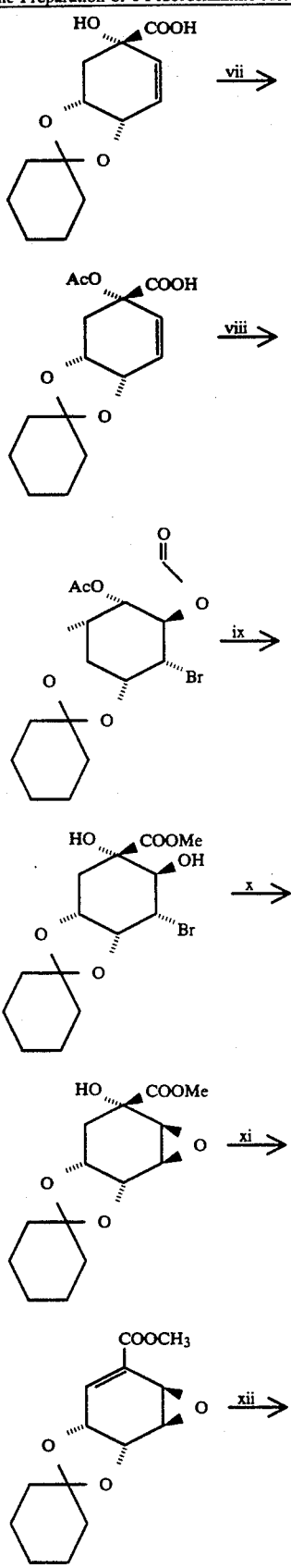

-continued
The Preparation of 6-Fluoroshikimic Acid

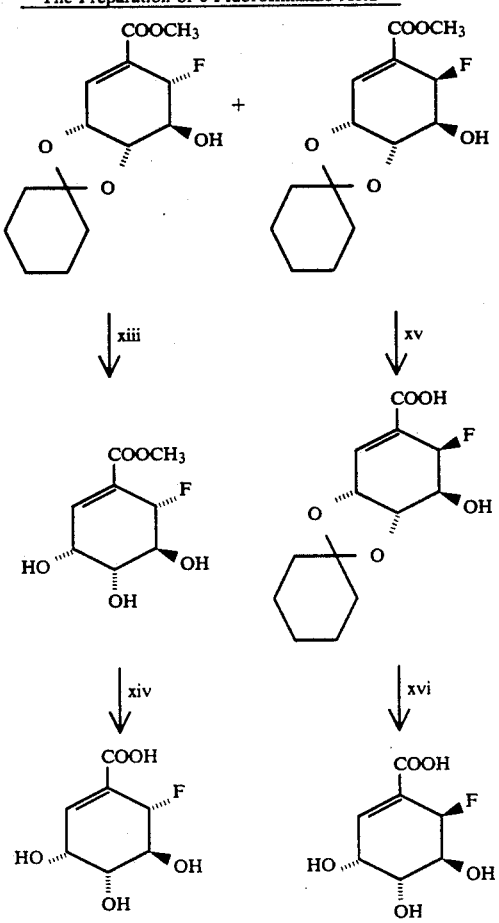

Notes i) cyclohexanone, benzene (or toluene), DMF; Amberlite Resin IR 120H; 83%
ii) NaH; $CH_2Cl_2$, $PhCH_2OCOCl$, $Bu_4NI$; 92%;
iii) NaOMe; 81%;
iv) $(CF_3SO_3)_2O$, pyridine, $CH_2Cl_2$; 96%;
v) $CHCl_3$, DBU;
vi) aq.KOH, dioxan;
vii) $Ac_2O$, pyridine, $CH_2Cl_2$;
viii) THF, $NaHCO_3$, pyridinium bromide perbromide, $H_2O$, $CH_2Cl_2$; (68% over 3 stages);
ix) MeOH, $CH_2Cl_2$, NaOMe; 75%;
x) $(BU)_4NOAc$, DMF; 82%;
xi) $[PhC(CF_3)_2O]SPh_2$ Martin's reagent; 87%;
xii) HF/pyridine;
xiii) TFA, $CH_2Cl_2$, $H_2O$;
xiv) 6N HCl, 65° C., 5 hr. Product purified on Dynamax $C_{18}$ column, 99.9% $H_2O$, 0.1% TFA;

-continued
The Preparation of 6-Fluoroshikimic Acid xv) LiOH, $H_2O$, dioxan, RT 1 hr. Mixture partitioned between EtOAc/$H_2O$.
Aqueous layer freeze dried;
xvi) TFA, $CH_2Cl_2$, RT 1 hr. Product purified
a) $C_{18}$ Dynamax column 20% $CH_3CN$ 80% $H_2O$;
b) $C_{18}$ Dynamax column 99.9% $H_2O$ 0.1% TFA;

EXAMPLE 3

(3R,4R,5S,6S)6-α-Fluoroshikimate-3-phosphate

Tris buffer (10mM)(pH8), adenosine triphosphate (4mM), magnesium chloride (10mM, 6-α-fluoroshikimate (5mM) and shikimate kinase (0.75 units) in a reaction volume of 1 ml were incubated for 2 hours at 37° C. The reaction mixture, on completion of the incubation period was filtered through (centrifiguration) a Centricon 10,000 Dalton molecular weight cut-off filter. In this way the high molecular weight enzyme and protein impurities were removed. The filtrate was freeze-dried and re-dissolved in $D_2O$ for analysis by nuclear magnetic resonance spectroscopy. This showed a 55% conversion to the title compound. NMR ($D_2O$) 4.18(1H,m,$H_5$); 4.82(1H,m,$H_3$); 5.21(1H,dd,$H_6$); 6.58(1H,d,$H_2$) (signal for $H_4$ obscured by $D_2O$).

We claim:
1. A compound of the formula (II):

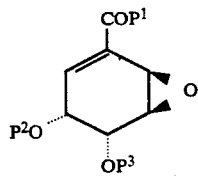

wherein
$P^1$ is a group $R^1$, wherein $R^1$ is hydroxy or a moiety biotransformable thereto, or is a protected derivative thereof;
$P^2$ is a protecting group; and
$P^3$ is a protecting group.
2. A compound according to claim 1 wherein $P^1$ is hydroxy.
3. A compound according to claim 1 wherein $P^1$ is a moiety biotransformable to hydroxy.
4. A compound according to claim 1 wherein $P^1$ is protected hydroxy.
5. A compound according to claim 1 wherein $P^2$ and $P^3$ are independently selected from lower alkanoyl, lower alkoxycarbonyl, haloloweralkoxycarbonyl, arylloweralkoxycarbonyl, triloweralkylsilyl and aryl lower alkyl; or $P^2$ and $P^3$ together complete an acetal ring system.
6. A compound according to claim 5 wherein $P^2$ and $P^3$ together complete a methylenedioxyacetal, benzylideneacetal or cyclohexylideneacetal.

* * * * *